Jan. 19, 1954 G. MERRILL Plant Pat. 1,245

PEACH TREE

Filed Feb. 9, 1953

WITNESS

Madison L. Avery

INVENTOR

Grant Merrill by [illegible]

ATTYS.

Patented Jan. 19, 1954 Plant Pat. 1,245

UNITED STATES PATENT OFFICE 1,245

PEACH TREE

Grant Merrill, Red Bluff, Calif.

Application February 9, 1953, Serial No. 336,025

1 Claim. (Cl. 47—62)

The present invention is directed to a new and distinct variety of peach tree which bears large, firm, highly colored, freestone fruit.

By comparison with the Redhaven variety of peach (unpatented), which it generally resembles, the present variety is distinguished, as to novelty, by a tree which is larger, and by moderate setting of the fruit and ready sizing; these latter characteristics being of importance, as large, commercially desirable fruit results from normal pruning and thinning of the tree. The present variety thus avoids the fault of the Redhaven peach which sets very heavy crops, making it difficult, even with extreme pruning and thinning, to obtain fruit of the large size required for the market.

The fruit of the two varieties are otherwise generally similar, including high coloring, firmness when ripe, and having substantially the same ripening period.

Another distinguishing characteristic of the present variety of peach tree is that its fruit takes on a high gloss or polish when run through the cleaning brushes preparatory to packing and shipping.

The instant variety of peach tree was originated by me in a breeding plot on my ranch near Red Bluff, County of Tehama, California, in the following manner:

The J. H. Hale (unpatented) peach was crossed with the Redbird peach (unpatented), and seeds from such cross were gathered and subsequently planted. Of the resulting seedlings, which were permitted to open-pollinate, the most promising were selected. Seeds from such selected seedlings were then gathered and planted, and the instant variety is one of the seedlings which resulted; it having been recognized by me—upon careful observation—that such one seedling gave particular promise, with respect to its commercial potentialities, due to the novel characteristics hereinbefore described.

Subsequent to origination of the variety in the above manner, I successfully reproduced it by budding onto Lovell peach (unpatented) seedlings in a test plot on my ranch located as aforesaid. These reproductions were found, upon exacting comparison, to carry forward each and every one of the novel characteristics of the parent tree.

Figure 1:
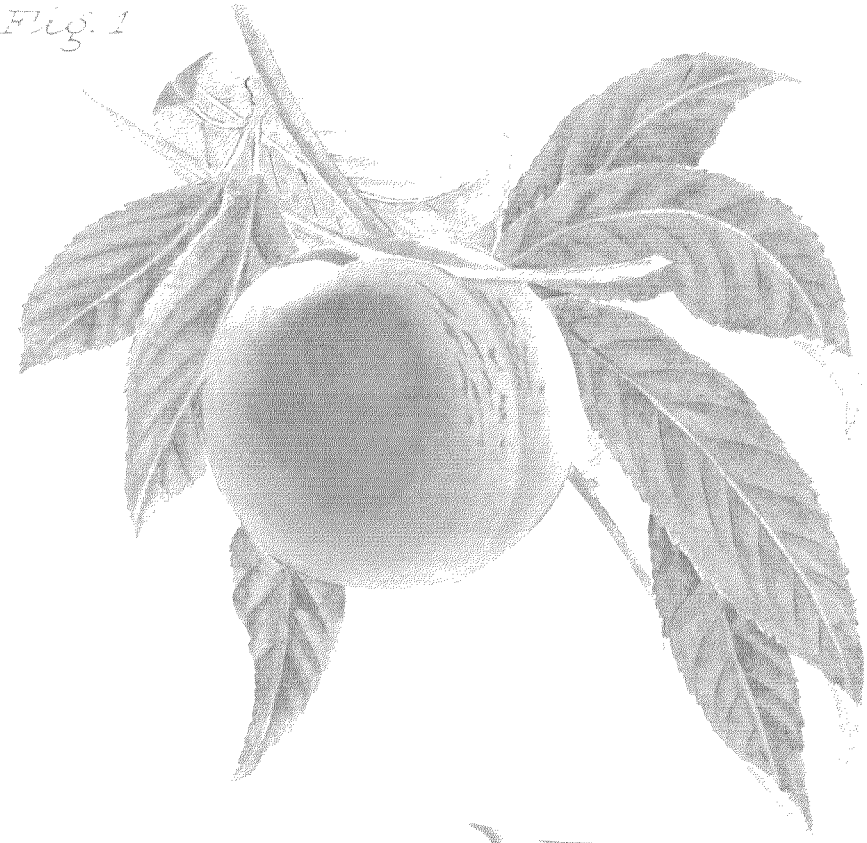
Fig. 1 is an elevation of one of the fruit of the new and distinct variety, together with twigs and leaves.
Figure 2:
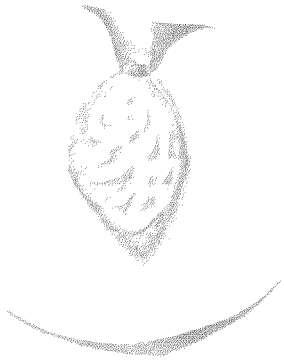
Fig. 2 is a sectional elevation of one of the fruit, with the stone exposed but remaining in place.

Referring now more specifically to the pomological details of this new and distinct variety of peach tree, the following is an outline description thereof; all major color plate identifications being by reference to Maerz and Paul Dictionary of Color:

Tree: Large; vigorous; upright; open; vasiform; medium productiveness; regular bearer.

Trunk: Stocky; medium shagginess.

Branches: Medium slenderness; medium shagginess.

*Color.*—Gray-brown (7–E–3).

*Lenticels.*—Medium quantity; medium size.

Leaves: Medium size. Length—6⅝″ to 8$\frac{1}{16}$″, average 7$\frac{23}{32}$″; width—1¾″ to 2″, average 1$\frac{17}{32}$″. Lanceolate shape; acuminately pointed; medium thickness; smooth to slightly rugose.

*Color.*—Top side—medium green (23–L–7). Under side—lighter green (20–E–3).

*Margin.*—Finely crenate.

*Petiole.*—Medium length; medium thickness.

*Glands.*—One to four, average three. Alternate arrangement; medium size; reniform. Yellow green in July, red in November. On petiole and leaf base.

*Stipules.*—On new growth, dropping off early.

Flower buds: Medium size; medium length. Obtuse shape; free; pubescent.

Flowers: Date of first bloom at Red Bluff, California, March 10th. Date of last bloom at Red Bluff, California, March 22nd. Midseason; medium size; pink to light red.

Fruit: First picking at Red Bluff, California, June 26, 1952. Last picking at Red Bluff, California, July 3, 1952.

*Size.*—Uniform; large. Average diameter axially—$\frac{13}{16}$″; average transverse in suture plane—2$\frac{29}{32}$″; average cheek to cheek, 2$\frac{29}{32}$″.

*Form.*—Uniform; slightly symmetrical; nearly globose.

*Suture.*—Distinct line. Extends from base to beyond apex. Some depression beyond pistil point.

*Ventral surface.*—Rounded strongly; lipped throughout both sides; lips slightly unequal.

*Cavity.*—Flaring; elongated in suture plane, with tendency of suture to show on both sides. Average depth — ⅝″; average breadth—$\frac{23}{32}$″. Markings—yellow, with red streaks down to base in many fruits.

*Base.*—Truncate to slightly oblique.

*Apex.*—Short; truncate. Pistil point—oblique.

Skin: Thin; medium tough to tender; non-astringent or bitter. Tenacious to flesh when firm; when soft will separate easily.

*Tendency to crack.*—None.

*Down.*—Scant; rolls up when rubbed. Medium length.

*Color.*—Bright yellow under-color (11–L–6 shading to 10–L–9), with a light to medium reddish blush (4–J–12 shading to 7–L–6 over most of the surface, with darker red patches or streaks (4–L–10) on the surface exposed to the sun.

Flesh:

*Color.*—Yellow (10–L–6), slightly reddish near stone (1–B–11, shading to 1–K–10).

*Surface of pit cavity.*—Greenish yellow with a very slight reddish streak along ventral surface—whitish yellow fiber ends.

*Amygdalin.*—Moderate.

*Juice.*—Moderately rich.

*Fibres.*—Abundant; coarse; tough; long.

*Ripens.*—Evenly.

*Flavor.*—Acid; delicate; fruity.

*Aroma.*—Distinct.

*Eating quality.*—Excellent. Remains firm until nearly over-ripe.

Stone: Free when ripe, parts from flesh smoothly.

*Fibres.*—Long. Retains fibre-like threads along ventral ridge.

*Size.*—Medium. Average length—$1\frac{17}{32}''$; average breadth—$1\frac{1}{32}''$; average thickness—$\frac{13}{16}''$.

*Form.*—Ovoid, cuneate towards base.

*Base.*—Oblique.

*Hilum.*—Oval.

*Apex.*—Acute.

*Sides.*—Equal to slightly unequal.

*Surface.*—Regularly furrowed.

*Ridges.*—Rounded toward apex.

*Pits.*—Elongated.

*Ventral edge.*—Medium thickness, with wing towards base.

*Dorsal edge.*—Full, with deep grooves towards base to above center, ridges on either side interrupted.

*Tendency to split.*—None.

*Color.*—Light reddish brown (11–G–7).

Use: Long distance shipment; local market; dessert; canning; freezing.

Keeping quality: Excellent.

Shipping quality: Excellent.

The tree and its fruit herein described may vary in slight detail due to climatic and soil conditions under which the variety may be grown.

Having thus described my invention, I claim:

A new and distinct variety of peach tree, substantially as described and illustrated, bearing large, firm, highly colored, freestone fruit; characterized—as to novelty, and as compared to the heavy setting, difficult to size, Redhaven peach—by a larger tree, and by setting moderately and sizing readily with normal pruning and thinning; the fruit of the two varieties being otherwise generally similar, including substantially the same ripening period.

GRANT MERRILL.

No references cited.